United States Patent [19]

Carpenter

[11] Patent Number: 4,586,491

[45] Date of Patent: May 6, 1986

[54] BRONCHOSCOPE WITH SMALL GAUGE VIEWING ATTACHMENT

[75] Inventor: George J. Carpenter, Southbridge, Mass.

[73] Assignee: Warner-Lambert Technologies, Inc., Morris Plains, N.J.

[21] Appl. No.: 681,460

[22] Filed: Dec. 14, 1984

[51] Int. Cl.⁴ .............................................. A61B 1/06
[52] U.S. Cl. ...................................................... 128/6
[58] Field of Search ...................... 128/4, 6, 10, 11, 5, 128/7

[56] References Cited

U.S. PATENT DOCUMENTS

| | | | |
|---|---|---|---|
| 4,041,936 | 8/1977 | Carden | 128/6 |
| 4,258,721 | 3/1981 | Parent et al. | 128/6 X |
| 4,269,192 | 5/1981 | Matsuo | 128/6 X |

*Primary Examiner*—William H. Grieb
*Attorney, Agent, or Firm*—R. S. Strickler; A. H. Spencer

[57] ABSTRACT

A bronchoscope with usual and customary accessories such as working channels for irrigation, forceps, light and image fiber optic bundles where one channel is adapted to receive a small gauge catheterscope for reaching, viewing and inspecting remote small diameter bronchioli of a bronchial tree.

4 Claims, 4 Drawing Figures

U.S. Patent  May 6, 1986  4,586,491
FIG.1
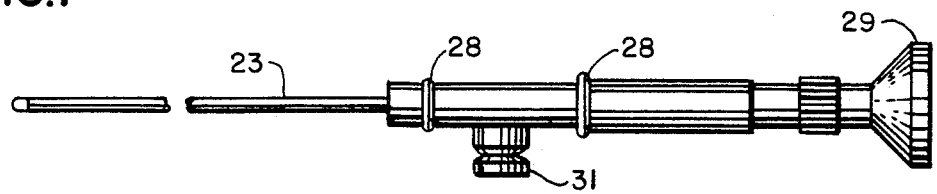
FIG.1A
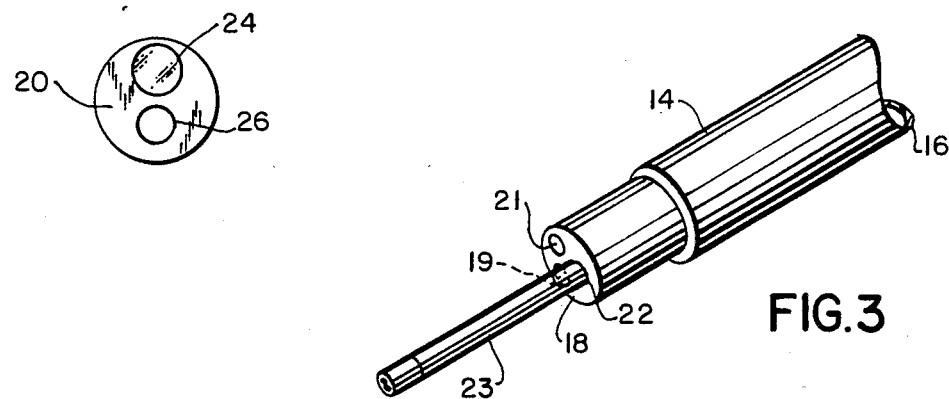
FIG.3
FIG.2
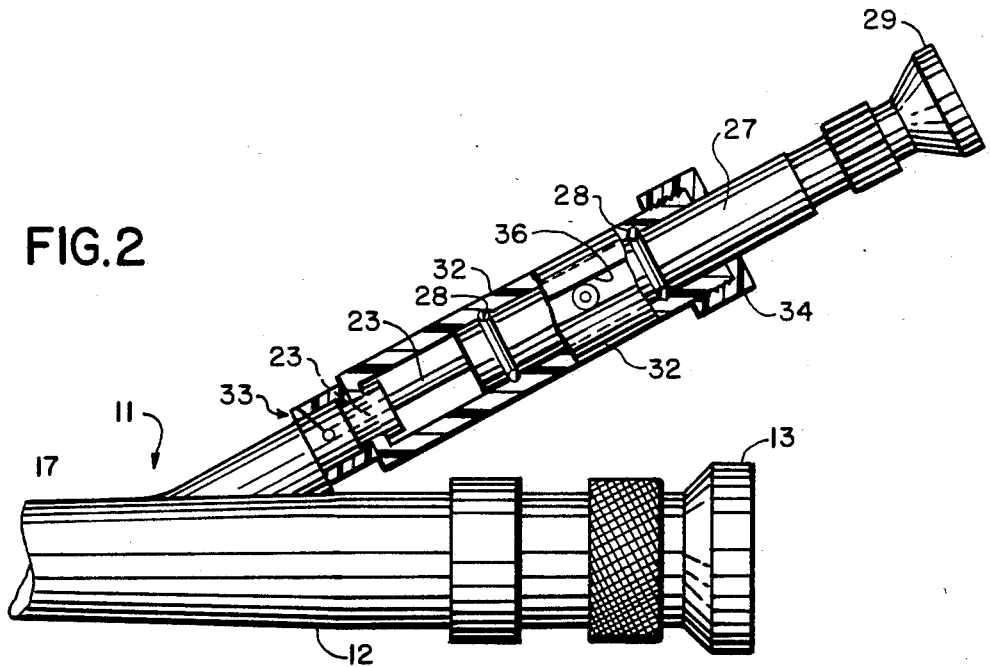

BRONCHOSCOPE WITH SMALL GAUGE VIEWING ATTACHMENT

BACKGROUND OF THE INVENTION

The present invention relates to fiberscopes such as bronchoscopes used to make internal inspections of the bronchial tree in medical or veterinary situations.

In usual and customary fashion, bronchoscopes include image and light guide fiber optic systems as well as mechanisms for articulating the distal end of a scope shaft as the shaft is advanced into the bronchial tree. The scopes also include one or more through channels for irrigation, suction or biopsy.

Although prior art bronchoscopes have flexible shafts of small diameter, i.e., of the order of 0.200 to 0.250 inches, they exhibit definite limitations when a bronchoscopist wishes to probe the most remote bronchioli near the ends of branches of the bronchial tree.

SUMMARY OF THE INVENTION

Consequently, it is a special feature of the present invention to provide a bronchoscope which is useful to inspect the most remote reaches of the bronchial tree.

A still further feature of the invention is the provision of a catheterscope having a diameter of the order of 0.066 to 0.110 inches which can be received within a vacant channel of a bronchoscope and which includes a light guide and an image-transmitting fiber optic bundle.

A further feature of the invention is the provision of a catheterscope housed movably within the shaft of a bronchoscope where the catheterscope can be advanced beyond the distal end of the bronchoscope under the control of the articulation system of the bronchoscope whereby a bronchoscopist can probe the small diameter remote branches of the bronchial tree.

A bronchoscope embracing certain features of the present invention may comprise a bronchoscope shaft having an open channel of a given length extending from a distal end to a proximal end of the shaft and a catheterscope having a small diameter shaft of a greater length than said given length received in said open channel and movable within said channel beyond the distal end of said bronchoscope shaft operable to penetrate small diameter remote branches of bronchioli of the bronchial tree.

Other features and advantages of the present invention will become more apparent from an examination of the succeeding specification when read in conjunction with the appended drawings, in which;

BRIEF DESCRIPTION OF THE DRAWINGS

FIG. 1 is a schematic illustration of a catheterscope embracing the present invention;

FIG. 1A shows the distal end of the catheterscope;

FIG. 2 shows, schematically, a portion of a bronchoscope with a catheterscope in place; and FIG. 3 shows the catheterscope projecting beyond the distal end of the shaft of the bronchoscope.

DESCRIPTION OF THE PREFERRED EMBODIMENT

The reference numeral 11 indicates generally a bronchoscope having a housing 12, an eyepiece 13 and a flexible shaft 14 broken away from housing 12 as at 16 and 17.

The distal end 18 of flexible shaft 14 shows a conventional image-transmitting fiber optic bundle 19 and a light guide bundle 21.

Open through channel 22 is shown receiving a catheterscope shaft 23 projecting beyond the distal end 18 of the flexible bronchoscope shaft 14.

The diameter of the shaft 14 is of the order of 0.200 to 0.250 inches while the diameter of the catheterscope shaft 23 is of the order of 0.066 to 0.110 inches.

As is most apparent in FIGS. 1 and 1A, the distal end 20 of the catheterscope shaft 23 includes an image-transmitting system 24 and a light guide 26.

The shaft 23 is received in a piston 27 having spaced rubber or the like O-rings 28—28 and the image system terminates at eyepiece 29.

The light guide 26 leads to a receptacle 31 to which an appropriate light source (not shown) is connected in any suitable fashion.

The piston 27 is received in a tubular housing 32 which makes a suitable quick-release connection with the bronchoscope housing 12 as indicated by the reference numeral 33 in FIG. 2. A bayonet-type connection is suitable.

With the shaft 23 of the catheterscope fed into the channel 22 of the shaft 14, the O-rings 28—28 engage the interior of the tubular housing 32 and provide sufficient friction to retain the distal end of the catheterscope shaft in a desired position relative to the distal end of the bronchoscope shaft. Normally the distal ends 18 and 20 are flush initially.

A threaded cap 34 retains the piston 27 within housing 32 while elongated slot 36 provides clearance for the light source receptacle 31 as the piston 27 is advanced by depressing eyepiece 29 to project the distal end 20 of the catheterscope beyond the distal end 18 of the bronchoscope as shown in FIG. 3. The cooperation between the slot 36 and the light receptacle 31 provides a keying action and prevents the catheterscope from rotating.

In operation, a bronchoscopist inserts the shaft 14 into the bronchial tree in conventional fashion with the distal ends of both shafts flush with one another. The progress of the shaft 14 into the bronchial tree is observed through eyepiece 13.

When small bronchioli are reached that are too small to receive shaft 14, the bronchoscopist advances the small shaft 23 by depressing eyepiece 29 beyond the distal end of the large shaft and observes the interior of small bronchioli through the catheterscope eyepiece 29.

Articulation of the catheterscope is accomplished by the bronchoscope articulation system (not shown).

It is anticipated that a wide variety of modifications may be devised in the present invention without departing from the spirit and scope thereof.

What is claimed is:

1. A bronchoscope having image and light guide fiber optic bundles for internal inspection of a bronchial tree in medical and veterinary situations comprising:
    a bronchoscope shaft having an open channel of a given length extending from a distal end to a proximal end of the shaft and a catheterscope having a small diameter shaft of a greater length than said given length received in said open channel and movable within said channel beyond the distal end of the bronchoscope shaft operable to penetrate small diameter remote branches of bronchioli of the bronchial tree, said bronchoscope and said catheterscope having individual housings making a releasable connection one to the other, said catheterscope housing being tubular enclosing a piston connected to the catheterscope shaft, said piston being movable within said housing to advance and retract said catheterscope shaft relative to said bronchoscope shaft.

2. The bronchoscope of claim 1 in which the piston includes at least one resilient O-ring for establishing friction between the tubular housing and the piston.

3. The bronchoscope of claim 1 in which the catheterscope shaft terminates at one end in an eyepiece.

4. The bronchoscope of claim 3 in which the eyepiece is connected to the piston and is movable to drive the piston.

* * * * *